United States Patent
Culombo et al.

(10) Patent No.: US 6,190,405 B1
(45) Date of Patent: Feb. 20, 2001

(54) FLEXIBLE EXPANDABLE VASCULAR SUPPORT

(75) Inventors: Antonio Culombo, Gallarate (IT); Norbert Heise, Warendorf (DE)

(73) Assignee: GFE Corporation for Research and Development Unlimited, Warendorf (DE)

( * ) Notice: Under 35 U.S.C. 154(b), the term of this patent shall be extended for 0 days.

(21) Appl. No.: 09/230,617

(22) PCT Filed: May 28, 1998

(86) PCT No.: PCT/EP98/03148

§ 371 Date: May 25, 1999

§ 102(e) Date: May 25, 1999

(87) PCT Pub. No.: WO98/53763

PCT Pub. Date: Dec. 3, 1998

(30) Foreign Application Priority Data

May 28, 1997 (DE) .............................. 197 22 384

(51) Int. Cl.[7] ........................................ A61F 2/06
(52) U.S. Cl. ............................................. 623/1.15
(58) Field of Search .................. 623/1.15, 1.16, 623/1.17, 1.18, 1.19, 12.2, 1.21

(56) References Cited

U.S. PATENT DOCUMENTS

| | | | |
|---|---|---|---|
| 5,507,771 | * 4/1996 | Gianturco | 606/198 |
| 5,868,781 | * 2/1999 | Killion | 606/198 |
| 5,964,798 | * 10/1999 | Imran | 623/1.15 |
| 6,019,789 | * 2/2000 | Dinh et al. | 623/1.15 |
| 6,077,296 | * 6/2000 | Shokoohi et al. | 623/1 |

* cited by examiner

*Primary Examiner*—V. Millin
*Assistant Examiner*—Alvin Stewart
(74) *Attorney, Agent, or Firm*—Woodbridge & Associates, P.C.; Richard C. Woodbridge

(57) ABSTRACT

The invention relates to an expandable insert for use as a vessel support in blood vessels, the insert being able to deform plastically from a nonexpanded state to an expanded state by application of a radial force directed from the inside outward, with at least one tubular, essentially cylindrical main body section, whose circumferential surface is formed by a number of annularly meandering rings, the rings in each case forming a one-piece strand of material with a defined strand length. The insert is particularly stiff with respect to externally acting radial forces because a first group of rings is provided whose strand length essentially corresponds to the circumference of the insert in the expanded state, and a second group of rings is provided whose strand length is greater than the circumference of the insert in the expanded state.

10 Claims, 1 Drawing Sheet

FLEXIBLE EXPANDABLE VASCULAR SUPPORT

The invention relates to an expandable insert having the features of the preamble of claim 1.

Such inserts, also called stents, are known from U.S. Pat. No. 5,102,417 and from U.S. Pat. No. 5,195,984.

The known inserts have three tubular sections or segments which are made of an implantable material. The three tubular segments are each connected to one another via bridge members which are intended to allow the segments to tilt or cross in relation to each other.

The individual segments are formed by cutting out rectangular blanks from the jacket of the tubular segments. Blanks adjacent to each other in the circumferential direction are offset in relation to one another. The rectangular blanks have axially parallel long sides and narrow sides running in the circumferential direction. The narrow sides at the ends are not interconnected, so that due to free spaces the end face of the tubular segment has a crenelated appearance. In the known inserts, the interconnected segments are oriented coaxial to one another in the state when the insert is not in use, and they are connected by bridges between the narrow sides at the ends. In U.S. Pat. No. 5,102,417, straight, parallel bridge members run obliquely from one end face of a segment in the direction toward the narrow side adjacent to the opposite narrow side in the circumferential direction. Each narrow side of a segment is connected to a narrow side of the adjacent section, so that the obliquely extending bridge members give the insert a twisted appearance.

U.S. Pat. No. 5,195,984 discloses an insert in which adjacent segments are in each case connected via a straight, axially parallel bridge between two exactly opposite narrow sides. Between each segment there is only one bridge member, so that the space between the segments remains essentially free.

In practice, these inserts, with small material thicknesses, are not sufficiently stiff with respect to compression in the radial direction.

The object of the invention is therefore to provide an expandable insert for use as a vessel support in blood vessels, in which, together with sufficient flexibility for adaptation to the curvatures of the vessels, there is a particularly high level of resistance (recoil) to forces exerted radially from the outside.

This object is achieved by means of an expandable insert having the features of claim 1.

Because a first group of rings is provided whose strand length essentially corresponds to the circumference of the insert in the expanded state and a second group of rings is provided whose strand length is greater than the circumference of the insert in the expanded state, the rings of shorter strand length can efficiently take up compression forces, while the rings of greater strand length cover relatively uniformly the interspaces which arise between the rings of the first group. The rings of the second group additionally permit a flexibility of the insert under bending stresses within the necessary range.

It is advantageous if the strand length of the second group is 1.2 to 2.0 times as great as the strand length of the first group, in particular 1.3 to 1.5 times as great, because under these conditions a good relationship is obtained between expandability and shortening of length during expansion. Increased flexibility in relation to bending stresses is obtained if the strand length of the second group is 1.7 to 1.9 times as great as the strand length of the first group.

An arrangement with good coverage of the interspaces which arise is obtained if the meandering strands of the second group have length sections which in the nonexpanded state run parallel to the center axis of the main body. In addition, with regard to stability, it is advantageous if the meandering strands of the first group have circumferential sections which in the nonexpanded state run in the circumferential direction of the main body.

A particularly advantageous construction is obtained if the strands of the first group and the strands of the second group each intersect in the area of the length sections, in particular if the circumferential sections of the first group are connected centrally to the length sections of the second group.

A very uniform pattern of opening of the insert in the expanded state is obtained if the number of the periodically recurring meanderings of a strand of the first group is twice as great as the number of meanderings of a strand of the second group, for example if the meanderings of the first group have three or four periodic segments and the meanderings of the second group correspondingly have six or eight periodic segments.

An illustrative embodiment of the invention is set out below with reference to the drawing, in which:

FIG. 1 shows the unwound circumferential surface of a cylindrical, tubular vessel support in the nonexpanded state.

Figure 1:
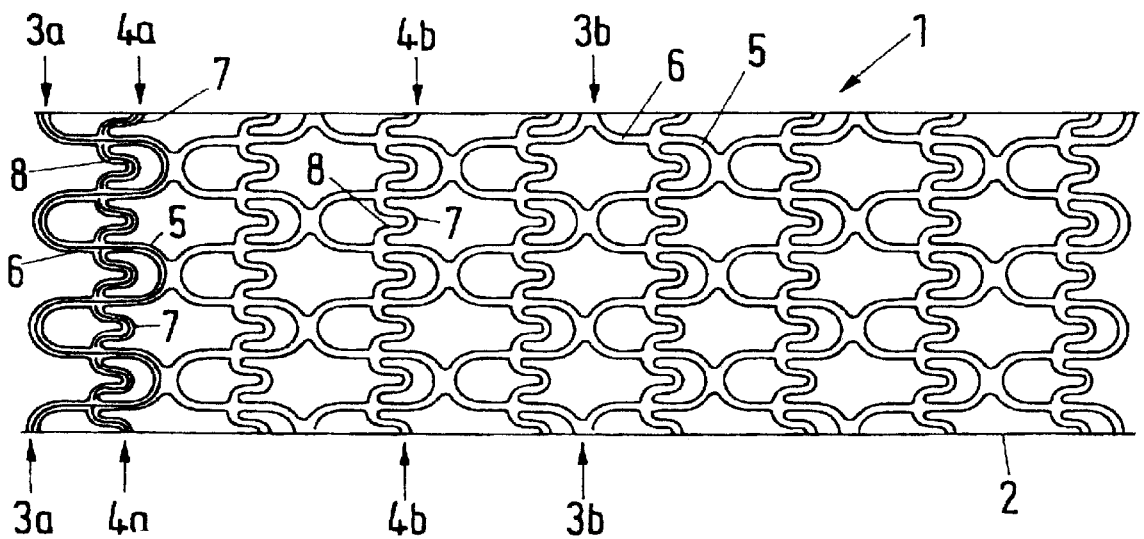
FIG. 1 shows the unwound circumferential surface of an expandable vessel support in the nonexpanded state.

The circumference section 1 is shown in a plan view, with the main body, which is cylindrical and tubular per se, being shown sectioned along an axis-parallel cutting plane 2 and spread out flat. The circumferential surface is made up of a number of meandering material strands 3a, b and 4a, b. The material strands 3a and 3b are looped in a meandering or undulating configuration in the circumferential direction of the insert, almost semicircular curve sections 5 alternating with straight, axis-parallel length sections 6. In the illustrative embodiment according to FIG. 1, the strand length of the encircling material strand 3a or 3b is approximately 14.5 mm, which, in the configuration shown, gives a diameter of 1.8 mm in the nonexpanded state. The meandering strand 3a or 3b can be considered as a periodically recurring form, each period comprising two length sections 6 and two curve sections 5. In this illustrative embodiment, therefore, there are three periodic areas arranged in the circumferential direction.

The material strands 4a and 4b are likewise arranged in a meandering configuration around the circumferential direction. Here too, curve sections 7 alternate with length sections 8, the length sections 8 in the nonexpanded state of the insert running approximately parallel to the length sections 6 of the material strands 3a and 3b. The material strands 4a and 4b also have a periodicity, the number of periods in this illustrative embodiment being twice as great as the number of periods of the material strands 3a, 3b. In FIG. 1, the illustrative embodiment has six periodic sections. In the present illustrative embodiment, the length of the material strands 4a, 4b is approximately 11 mm, which again, in the present configuration, leads to a diameter of 1.8 mm.

In the present illustrative embodiment, the material strands 3a and 3b pass through each other approximately centrally in the respective length section 6 of the material strand 3a, 3b. The material strands 4a, 4b here pass through the material strands 3a, 3b approximately at right angles.

In practice, the expandable insert according to the invention is cut as a single-piece element from a tube having the external diameter of 1.8 mm. A suitable material which can be used here is in particular implantable stainless steel, but other implantable materials can also be used. The material thickness in the radial direction is essentially constant over the entire area of the insert.

Figure 2:
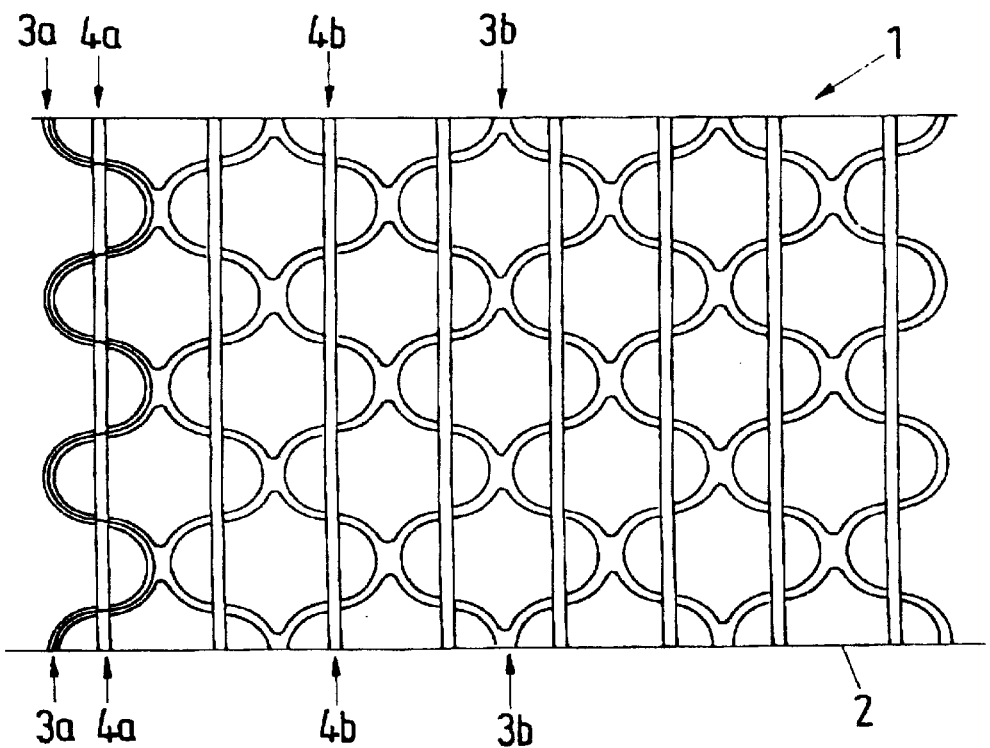
FIG. 2 shows the circumferential surface of an expandable vessel support according to FIG. 1 in the expanded state.

In FIG. 2, an insert according to FIG. 1 is shown in the second, expanded state. The diameter of the insert in the expanded state is 3.5 mm in this illustrative embodiment. The resulting deformation through using a force acting radially from the inside leads to the material strands 4a and 4b being fully stretched, i.e. forming in practice a circular ring of 11 mm circumference. In the present configuration, the longer material strands 3a and 3b are deformed into undulating, almost sinusoidal material strands.

The material strands 4a and 4b of circular ring shape in the expanded state provide a strong structural resistance to a radial force acting uniformly from the outside, which resistance reliably prevents collapse of the insert in the treated blood vessel. Alternatively, with the same resistance force (recoil), a smaller material thickness can be used compared to the known inserts. In both cases, the danger of renewed cross-sectional narrowing of the treated blood vessel, also called restenosis, is less than with the known inserts.

The use of the insert in practice is known in principle. When employed, the inserts according to the invention are introduced with a balloon catheter into the blood vessels that are to be treated. The balloon catheter is widened by injecting a fluid, whereupon the inserts expand permanently in the radial direction by means of plastic deformation.

After the balloon catheter has been removed, the insert remains in the blood vessel and is in a short time enclosed by the tunica intima.

Of course, other configurations also afford the advantages according to the invention. Thus, for example, Ω-shaped configurations are conceivable.

What is claimed is:

1. An expandable insert for use as a vessel support in blood vessels, the insert being able to deform plastically from a nonexpanded state to an expanded state by application of a radial force directed from the inside outward, with at least one essentially cylindrical main body section, whose circumferential surface is formed by a number of annularly meandering rings, the rings in each case forming a one-piece strand of material with a defined strand length, wherein a first group of rings is provided whose strand length essentially corresponds to the circumference of the insert in the expanded state, and a second group of rings is provided whose strand length is greater than the circumference of the insert in the expanded state.

2. The insert as claimed in claim 1, wherein the strand length of the second group is 1.2 to 2.0 times as great as the strand length of the first group.

3. The insert of claim 2, wherein the strand length of the second group is 1.3 to 1.5 times as great as the strand length of the first group.

4. The insert of claim 2, wherein the strand length of the second group is 1.7 to 1.9 times as great as the strand length of the first group.

5. The insert of claim 1, wherein the meandering strands of the second group have length sections which in the nonexpanded state run parallel to the center axis of the main body.

6. The insert of claim 1, wherein the meandering strands of the first group have circumferential sections which in the nonexpanded state run in the circumferential direction of the main body.

7. The insert of claim 1, wherein the strands of the first group and the strands of the second group each intersect in the area of the length sections.

8. The insert of claim 1, wherein the number of meanderings of each strand of the first group is twice as great as the number of meanderings of the corresponding strand of the second group.

9. The insert of claim 1, wherein the strands of the first group in the expanded state of the insert are stretched essentially to form a circular ring.

10. The insert of claim 1, wherein the strands in both groups of rings are contained entirely in the tubular circumferential surface.

* * * * *